United States Patent [19]

Helling et al.

[11] Patent Number: 4,939,263

[45] Date of Patent: Jul. 3, 1990

[54] CONTROL OF ISOMER DISTRIBUTION IN A CHLORINATION PROCESS

[75] Inventors: Richard K. Helling, Martinez; Philip D. Grover, Concord; Thomas J. Dietsche, Berkeley; Mark L. Garibaldi, Martinez, all of Calif.

[73] Assignee: The Dow Chemical Company, Midland, Mich.

[21] Appl. No.: 413,926

[22] Filed: Sep. 28, 1989

[51] Int. Cl.$^5$ .......................................... C07D 213/61
[52] U.S. Cl. ................................................. 546/345
[58] Field of Search ....................................... 546/345

[56] References Cited

U.S. PATENT DOCUMENTS

| | | | |
|---|---|---|---|
| 3,418,323 | 12/1968 | Johnston et al. | 546/345 |
| 3,732,230 | 5/1973 | Brewer et al. | 546/345 |
| 4,227,001 | 10/1980 | Dietsche et al. | 546/345 |
| 4,256,894 | 3/1989 | Dietsche et al. | 546/345 |
| 4,487,935 | 12/1984 | Marinak et al. | 546/345 |
| 4,564,681 | 1/1986 | Marinak et al. | 546/345 |
| 4,577,027 | 3/1986 | Marinak et al. | 546/345 |
| 4,701,532 | 10/1987 | Humphreys et al. | 546/345 |

Primary Examiner—Richard A. Schwartz
Assistant Examiner—J. Haley
Attorney, Agent, or Firm—D. Wendell Osborne

[57] ABSTRACT

The relative amounts of 5,6-dichloro-2-(trichloromethyl)pyridine and 3,6-dichloro-2-(trichloromethyl)pyridine obtained in the chlorination of 2-chloro-6-(trichloromethyl)pyridine in the liquid phase at temperatures of about 160° C. to about 220° C. and in the presence of a metal halide catalyst, such as ferric chloride, are controlled by regulating the amount of hydrogen chloride present in the system, adding hydrogen chloride to obtain a mixture enriched in 5,6-dichloro-2-(trichloromethyl)pyridine or removing hydrogen chloride, usually by passing excess chlorine or an inert gas through the system, to obtain a mixture enriched in 3,6-dichloro-2-(trichloromethyl)pyridine.

12 Claims, No Drawings

CONTROL OF ISOMER DISTRIBUTION IN A CHLORINATION PROCESS

BACKGROUND OF THE INVENTION

The present invention relates to a process for controlling the isomer distribution of the chlorination products obtained in the liquid phase chlorination of 2-chloro-6-(trichloromethyl)pyridine by regulating the concentration of hydrogen chloride in the system.

The chlorination of 2-chloro-6-(trichloromethyl)pyridine in the liquid phase at elevated temperatures is disclosed in U.S. Pat. No. 4,256,894 to produce 3,6-dichloro-2-(trichloromethyl)pyridine and 5,6-dichloro-2-(trichloromethyl)pyridine as well as higher chlorination products, such as 2,3,4,5-tetrachloro-6-(trichloromethyl)pyridine, 2,3,5,6-tetrachloropyridine, and pentachloropyridine. Hydrogen chloride is a by-product. Catalysts, such as metal halides, especially ferric chloride, are often employed. Application of this process to the preparation of either 3,6-dichloro-2-(trichloromethyl)pyridine or 5,6-di-chloro-2-(trichloromethyl)pyridine specifically is deficient in that both of these two monochlorination products are always formed and there is no way reported to alter their ratio in favor of the isomer specifically desired.

Since the dichloro-6-(trichloromethyl)pyridine isomers are much more valuable as individual entities than as mixtures and because typically only one of the isomers is desired at any one time, methods of controlling the isomer distribution obtained in the chlorination are highly desirable. 3,6-Dichloro-2-(trichloromethyl)pyridine is useful as an intermediate in the production of 3,6-dichloropicolinic acid, a commercial herbicide, and other valuable compounds. 5,6-Dichloro-2-(trichloromethyl)pyridine is similarly useful as a chemical intermediate for agricultural chemicals and pharmaceuticals.

SUMMARY OF THE INVENTION

It has now been found that the ratio of 5,6-di-chloro-2-(trichloromethyl)pyridine to 3,6-dichloro-2-(trichloromethyl)pyridine obtained on chlorination of 2-chloro-6-(trichloromethyl)pyridine in the liquid phase can be controlled by regulating the amount of hydrogen chloride present in the system.

The process of the invention includes an improved process for chlorinating 2-chloro-6-(trichloromethyl)pyridine in the liquid phase at elevated temperatures and in the presence of a metal halide catalyst to obtain a chlorination mixture containing 5,6-dichloro-2-(trichloromethyl)pyridine and 3,6-dichloro-2-(trichloromethyl)pyridine isomers, wherein the improvement comprises controlling the ratio of said isomer by regulating the amount of hydrogen chloride present in the system, adding hydrogen chloride to obtain a mixture enriched in 5,6-dichloro-2-(trichloromethyl)pyridine or removing hydrogen chloride to obtain a mixture enriched in 3,6-dichloro-2-(trichloromethyl)pyridine.

It is usually preferred to remove hydrogen chloride from the chlorination medium and obtain a mixture of dichloro-6-(trichloromethyl)pyridines enriched in 3,6-dichloro-2-(trichloromethyl)pyridine.

DETAILED DESCRIPTION OF THE INVENTION

In carrying out the present invention 2-chloro-6-(trichloromethyl)pyridine and chlorine are combined in the liquid phase under conditions conducive to monochlorination in a medium in which the concentration of hydrogen chloride is controlled by the addition or by removal of hydrogen chloride. A mixture containing as a primary product a combination of 3,6-dichloro-2-(trichloromethyl)pyridine (which could alternatively be named 2,5-dichloro-6-(trichloromethyl)pyridine) and 5,6-dichloro-2-(trichloromethyl)pyridine (which could alternatively be named 2,3-dichloro-6-(trichloromethyl)-pyridine), usually along with varying amounts of other polychloro-6-(trichloromethyl)pyridines, polychloropyridines, and unreacted 2-chloro-6-(trichloromethyl)-pyridine, is obtained. Hydrogen chloride is a by-product. When the desired monochlorination product is 5,6-dichloro-2-(trichloromethyl)pyridine, the chlorination is carried out in the presence of added hydrogen chloride so that the concentration of hydrogen chloride in the medium is greater than that which would have been present as a result of its formation as a by-product in the reaction. When 3,6-dichloro-2-(trichloromethyl)pyridine is the desired product, hydrogen chloride is removed from the system so that the concentration of hydrogen chloride in the medium is less than that which would have been present as a result of its formation as a by-product in the reaction.

Conditions conducive to the liquid phase chlorination of 2-chloro-6-(trichloromethyl)pyridine are essentially those described in U.S. Pat. No. 4,256,894, hereby incorporated by reference. The 2-chloro-6-(trichloromethyl)pyridine is generally heated in a pressure reactor with an effective catalyst and an amount of chlorine gas in excess of the theoretical amount in a manner such that good contact between the liquid and the chlorine gas is achieved. The mixture is generally agitated. Temperatures of about 160° C to about 220° C are satisfactory and temperatures of about 170° C to about 210° C are generally preferred. The pressure is maintained at just above atmospheric to about 1600 kiloPascals by allowing gases to escape through a vent as required. Pressures of about 130 to about 700 kiloPascals are preferred. The reaction is allowed to continue under these conditions until a significant amount of a mixture of dichloro-6-(trichloromethyl)pyridines is present, usually until over about half of the chloropicolines and chloropyridines in the mixture are dichloro-6-(trichloromethyl)pyridines. The amount of dichloro-6-(trichloromethyl)pyridines in the mixture goes though a maximum and then decreases, due to the formation of higher chlorinated products, as the chlorination is continued.

Lewis acid metal salts and precursors to Lewis acid metal salts are generally effective catalysts for the reaction. Typical Lewis acid salts that are effective include the halides of ruthenium, tantalum, tungsten, aluminum, zinc, and iron. Chlorides are preferred Ferric chloride is especially preferred. Typical precursors to Lewis acid metal salts include the metals, themselves, such as iron, aluminum, and zinc, and the corresponding metal oxides, such as alumina, and ferric oxide. The catalysts are employed in an effective amount. Generally, about 0.5 to about 20 mole percent based on the starting 2-chloro-6-(trichloromethyl)pyridine is a satisfactory amount.

About 1 to about 5 mole percent is preferred and about 1 to about 3 percent is more preferred.

The 2-chloro-6-(trichloromethyl)pyridine employed as a starting material is a well known compound having the common name nitrapyrin. It can be employed in the present invention in either essentially pure form or in the form of a mixture with other chlorinated alpha-picoline compounds or with suitable diluents.

The chlorination process can be carried out in a variety of ways including batchwise and continuous methods as is known in the art. Suitable continuous methods include those wherein multiple chlorination vessels connected in series are employed. It is often preferred to use a continuous process.

The products of the invention, 3,6-dichloro-2--(trichloromethyl)pyridine or 5,6-dichloro-2-(trichloromethyl)pyridine can be recovered from the chlorination mixture obtained in the present process by conventional methods, such as by distillation. Typically, a mixture enriched in a combination of the two products is first recovered by fractional distillation and then that mixture is separated into its individual components by further fractional distillation.

Hydrogen chloride can be removed from the chlorination medium in a variety of ways. Usually, it is removed as a gas though a vent in the pressure reactor Removal as a gas can be facilitated by the adding other gases to the system and controlling the pressure by simultaneously removing gases by means of the vent. The added gas can be excess chlorine or an inert diluent. Suitable diluent gases include nitrogen, argon, neon, helium, and carbon tetrachloride (a gas at the chlorination temperature). Generally, the more diluent gas or excess chlorine added, the more hydrogen chloride is removed. An enhanced amount of 3,6-di-chloro-2-(trichloromethyl)pyridine as compared with 5,6-dichloro-2-(trichloromethyl)pyridine is obtained whenever any of the hydrogen chloride formed in the reaction is removed. As a rule, the amount increases as the amount of hydrogen chloride removed increases. It is, therefore, preferred to remove as much of the hydrogen chloride by-product as is practical in view of the cost of doing so. The costs include the cost of the diluent and its disposal or recycle and the cost of heating the diluent. Generally, it is preferred to remove sufficient hydrogen chloride so that its concentration in the chlorination liquid is less than about 0.2 weight percent. It is more preferred to remove sufficient hydrogen chloride so that its concentration in the chlorination liquid is less than about 0.1 weight percent and most preferred to remove sufficient hydrogen chloride so that its concentration in the chlorination liquid is less than about 0.05 weight percent. This is accomplished when the concentration of hydrogen chloride in the vapor space above the chlorination liquid (same as the vent gas) is less than about 25 weight percent, about 20 weight percent, and about 10 weight percent, respectively. The average mole ratio of chlorine to hydrogen chloride during the process will typically be greater than about 5 in the liquid phase and greater than about 1.3 in the vapor phase (vent gas). The mole percent of hydrogen chloride in the liquid phase is preferably less than the mole percent of metal halide catalyst for this embodiment of the invention.

Hydrogen chloride can be added to the chlorination medium in a variety of ways. Usually, it is added as a gas either through a separate orifice or as a mixture with the chlorine added. It can also be "added" by adding a readily chlorinated compound to the medium and generating it *in situ*. An enhanced amount of 5,6-dichloro-2-(trichloromethyl)pyridine as compared with 3,6-dichloro-2-(trichloromethyl)pyridine is obtained whenever any hydrogen chloride is added to the medium. As a rule, the amount increases as the amount of hydrogen chloride added increases. It is, therefore, generally preferred to add as much of the hydrogen chloride as is practical in view of the cost of doing so. The costs include the cost of hydrogen chloride and its recycle as well as the cost of heating it. The addition of too large amounts further makes it difficult to maintain a sufficiently large chlorine concentration in the reactor to achieve a reasonable rate of chlorination. I is further preferred to add the hydrogen chloride to the reactor in a continuous manner, replacing at least a portion of any removed from the system in the vent gas. Generally, a total of at least about 0.25 mole of hydrogen chloride per mole of the 2--chloro-6-(trichloromethyl)pyridine present is added. It is preferred to add a total of at least about 1 mole of hydrogen chloride per mole of 2-chloro-6-(trichloromethyl)pyridine present and more preferred to add a total of at least about 2 moles of hydrogen chloride per mole of 2-chloro-6-(trichloromethyl)pyridine present. It is further preferred to add at least about one-third as much hydrogen chloride as chlorine in the process. The average mole ratio of chlorine to hydrogen chloride during the process will typically be less than about 5 in the liquid phase and less than about 1.3 in the vapor phase (vent gas). The mole percent of hydrogen chloride in the liquid phase is usually greater than the mole percent of metal halide catalyst for this embodiment of the invention.

Application of the present invention allows one to prepare 5,6-dichloro-2-(trichloromethyl)pyridine as the major dichloro-2-(trichloromethyl)pyridine along with co-product, 3,6-dichloro-2-(trichloromethyl)-pyridine in a ratio of up to about 10:1 5,6-dichloro-2--(trichloromethyl)pyridine to 3,6-dichloro-2-(trichloromethyl)pyridine. Conditions leading to a ratio of at least 4.5:1 are preferred. The method further allows one to prepare 3,6-dichloro-2-(trichloromethyl)pyridine as a leading dichloro-2-(trichloromethyl)pyridine along with co-product, 5,6-dichloro-2-(trichloromethyl)-pyridine in a ratio of up to about 1:1.9 3,6-dichloro-2--(trichloromethyl)pyridine to 5,6-dichloro-2-(trichloromethyl)pyridine. Conditions leading to a ratio of at least 1:2.2 are preferred.

The following example is presented to illustrate the invention. It should not be construed as limiting.

EXAMPLE

Chlorination of 2-Chloro-6-(trichloromethyl)pyridine in the Presence of Varving Amounts of Hydrogen Chloride Apparatus: A 1-liter Monel Parr pressure reactor (Model 4521) was employed which was fitted with a Monel gas inlet tube having a differential pressure transducer cell (DP cell) and a Badger Meter research control valve with P-7 Hastalloy trim which was attached separately to a chlorine reservoir and a nitrogen cylinder, a Monel gas inlet tube having a DP cell and a Badger Meter Research Control valve with P-7 Hastalloy trim which was attached separately to a hydrogen chloride cylinder and a nitrogen cylinder, a 0.64 centimeter (cm) diameter Monel double-block sampling tube with ball valves, a thermowell with thermocouple, a 7000 kiloPascal (kPa) rupture disc, an air motor-powered magnetic drive stirrer with pitched-blade turbines attached to the reactor head, and a vent tube with a Research Control air-to-close valve leading to an aqueous scrubbing column with a recirculation system containing 10 percent sodium hydroxide. An insulated Hoke 4HDM1000 1-liter high pressure sample cylinder was installed as a trap between each inlet and outlet tube and the reactor. The DP cells, which were used to keep the flows of chlorine and hydrogen chloride constant by means of a constant pressure drop across a 122 cm x 1.6 millimeter (mm) outside diameter nickel tubing capillary, were Validyne DP-15-30 cells equipped with 8.6 kPa rated diaphragms. Additional traps, filters, valves, and pressure release discs were installed as appropriate to protect the system from particulates and back-ups and for safety. The reactor was heated by means of a 1500-Watt Parr heater and, where necessary, the lines were heated with a heating tape or steam tracing and insulated with Nomex brand insulating wrap. The temperature, pressure, and gas inlet flows were controlled by computer. A 2-liter Monel Parr reactor having a copper-coil water jacket connected to a constant temperature bath was used as a chlorine reservoir. The chlorine reservoir and hydrogen chloride cylinder were placed on electronic Mettler balances so that their weights could be monitored.

Operating Procedure: Approximately 1100 grams (g) of about 90 percent purity 2-chloro-6-(trichloromethyl)-pyridine (containing 4,6-trichloro-2-(trichloromethyl)-pyridine as the major impurity along with small amounts of other chloropicolines and chloropyridines) was weighed and placed in the reactor. To this was added 1.0 weight percent (based on iron) of ferric chloride catalyst (approximately 33 g) and the reactor was closed. The chlorine reservoir was cooled to about 5° C, filled with up to 1800 g of liquid chlorine, and then heated to a temperature which would produce a pressure in the reservoir at least 275 kPa greater than that to be employed in the reactor (28° C when the reactor pressure was about 275 kPa). The reactor and the lines were heated to at least about 50° C and the stirrer was activated. Chlorine and, where desired, hydrogen chloride or nitrogen were then fed to the reactor, the reactor was heated to the desired temperature for the run, and then the automatic pressure control valve and flow control valves were set at the desired values for the run. When the temperature and pressure had stabilized to the desired values, an initial (0 time) liquid sample was withdrawn for analysis. Thereafter samples were taken about every 6 hours and were analyzed by standardized gas chromatography using a Hewlett Packard 5890A chromatograph with a thermal conductivity detector for chlorinated picolines and pyridines. The system was standardized to convert peak size to weight percent. The concentration of hydrogen chloride in the vapor phase and the liquid phase were calculated using the feed rates and the extent of reaction to determine total the total amount and the vapor-liquid equilibrium constant to determine the split between liquid and vapor phases.

Results: The results of several runs are given in the following tables.

SUMMARY OF REACTION CONDITIONS

| Run No. | Temp., °C. | Press., kPa | Total Gas Feed, g-moles/hour | Feed Gas Composition (Percent) | | |
|---|---|---|---|---|---|---|
| | | | | $Cl_2$ | HCl | $N_2$ |
| 1 | 200 | 1480 | 0.40 ± 0.02 | 100 | 0 | 0 |
| 2 | 200 | 1480 | 0.36 ± 0.07 | 55 | 45 | 0 |
| 3 | 175 | 380 | 0.22 ± 0.02 | 100 | 0 | 0 |
| 4 | 175 | 380 | 0.36 ± 0.06 | 19 | 81 | 0 |
| 5 | 175 | 380 | 0.37 ± 0.02 | 51 | 49 | 0 |
| 6 | 175 | 380 | 0.42 ± 0.09 | 76 | 24 | 0 |
| 7 | 175 | 380 | 0.37 ± 0.04 | 52 | 0 | 48 |
| 8 | 175 | 380 | 0.28 ± 0.07 | 62 | 0 | 38 |
| 9 | 175 | 380 | 0.44 ± 0.09 | 100 | 0 | 0 |
| 10 | 175 | 380 | 0.44 ± 0.14 | 79 | 0 | 21 |

CHLORINATION RESULTS

CHLORINATION MIXTURE COMPOSITION[1]

| Run No. | Time hours | 2-Cl-6-—CCl3—Pyridine (normalized), weight percent | 5,6-Isomer (normalized) weight percent | 3,6-Isomer (normalized) weight percent | HCl in Vapor Phase, weight percent[2] | HCl in Liquid Phase, weight percent[2] | 5,6:3,6 Isomer Ratio |
|---|---|---|---|---|---|---|---|
| 1 | 0 | 100.0 | 0.0 | 0.0 | | | — |
| | 6 | 63.2 | 25.1 | 5.3 | | | 4.7 |
| | 12 | 38.1 | 43.4 | 9.6 | | | 4.5 |
| | 24 | 3.3 | 62.5 | 12.0 | 30 | 0.21 | 5.2 |
| 2 | 0 | 100.0 | 0.0 | 0.0 | | | — |
| | 12 | 64.1 | 32.3 | 4.9 | | | 6.6 |
| | 24 | 35.2 | 50.4 | 6.8 | | | 7.4 |
| | 36 | 6.7 | 68.1 | 8.4 | 55 | 0.28 | 8.1 |
| 3 | 0 | 100.0 | 0.0 | 0.0 | | | — |
| | 24 | 73.4 | 16.5 | 7.4 | | | 2.2 |
| | 48 | 52.9 | 29.8 | 13.3 | 7 | 0.03 | 2.2 |
| 4 | 0 | 100.0 | 0.0 | 0.0 | | | — |
| | 24 | 95.7 | 2.3 | 0.3 | | | 7.7 |
| | 48 | 91.2 | 7.7 | 1.0 | 71 | 0.10 | 7.7 |
| 5 | 0 | 100.0 | 0.0 | 0.0 | | | — |

CHLORINATION RESULTS — continued

CHLORINATION MIXTURE COMPOSITION[1]

| Run No. | Time, hours | 2-Cl-6-—CCl$_3$—Pyridine (normalized), weight percent | 5,6-Isomer (normalized) weight percent | 3,6-Isomer (normalized) weight percent | HCl in Vapor Phase, weight percent[2] | HCl in Liquid Phase, weight percent[2] | 5,6:3,6 Isomer Ratio |
|---|---|---|---|---|---|---|---|
|  | 24 | 86.5 | 8.3 | 2.3 |  |  | 3.6 |

[1]Other identified compounds present in some samples are 2,3,6-trichloropyridine, 2,3,5,6-tetrachloropyridine, 2,3,4,6-tetrachloropyridine, pentachloropyridine, 2,4-dichloro-6-(trichloromethyl)pyridine, 4,5,6-trichloro-2-(trichloromethyl)pyridine, 3,5,6-trichloro-2-(trichloromethyl)pyridine, and 3,4,5,6-tetrachloro-2-(trichloromethyl)pyridine. The composition was normalized by treating all components other than 2-chloro-6-(trichloromethyl)pyridine present at the start of the run as diluents.
[2]Average for run, calculated.

CHLORINATION RESULTS

CHLORINATION MIXTURE COMPOSITION[1]

| Run No. | Time, hours | 2-Cl-6-—CCl$_3$—Pyridine (normalized), weight percent | 5,6-Isomer (normalized) weight percent | 3,6-Isomer (normalized) weight percent | HCl in Vapor Phase, weight percent[2] | HCl in Liquid Phase, weight percent[2] | 5,6:3,6 Isomer Ratio |
|---|---|---|---|---|---|---|---|
|  | 42 | 80.7 | 13.6 | 3.6 | 37 | 0.07 | 3.8 |
| 6 | 0 | 100.0 | 0.0 | 0.0 |  |  | — |
|  | 21 | 81.4 | 12.5 | 4.5 |  |  | 2.8 |
|  | 46 | 51.5 | 31.1 | 12.7 | 18 | 0.04 | 2.4 |
| 7 | 0 | 100.0 | 0.0 | 0.0 |  |  | — |
|  | 23 | 78.5 | 13.3 | 7.3 |  |  | 1.8 |
|  | 49 | 55.8 | 28.1 | 14.8 | 19 | 0.10 | 1.9 |
| 8 | 0 | 100.0 | 0.0 | 0.0 |  |  | — |
|  | 20 | 76.2 | 13.0 | 6.6 |  |  | 2.0 |
|  | 48 | 49.3 | 29.7 | 14.5 |  |  | 2.0 |
|  | 65 | 32.1 | 39.2 | 19.0 | 5 | 0.01 | 2.1 |
| 9 | 0 | 100.0 | 0.0 | 0.0 |  |  | — |
|  | 23 | 68.2 | 21.3 | 10.7 |  |  | 2.0 |
|  | 45 | 37.8 | 39.2 | 19.5 | 4 | 0.02 | 2.0 |
| 10 | 0 | 100.0 | 0.0 | 0.0 |  |  | — |
|  | 24 | 68.6 | 19.9 | 10.0 |  |  | 2.0 |

[1]Other identified compounds present in some samples are 2,3,6-trichloropyridine, 2,3,5,6-tetrachloropyridine, 2,3,4,6-tetrachloropyridine, pentachloropyridine, 2,4-dichloro-6-(trichloromethyl)pyridine, 4,5,6-trichloro-2-(trichloromethyl)pyridine, 3,5,6-trichloro-2-(trichloromethyl)pyridine, and 3,4,5,6-tetrachloro-2-(trichloromethyl)pyridine. The composition was normalized by treating all components other than 2-chloro-6-(trichloromethyl)pyridine present at the start of the run as diluents.
[2]Average for run, calculated.

CHLORINATION RESULTS

CHLORINATION MIXTURE COMPOSITION[1]

| Run No. | Time, hours | 2-Cl-6-—CCl$_3$—Pyridine (normalized), weight percent | 5,6-Isomer (normalized) weight percent | 3,6-Isomer (normalized) weight percent | HCl in Vapor Phase, weight percent[2] | HCl in Liquid Phase, weight percent[2] | 5,6:3,6 Isomer Ratio |
|---|---|---|---|---|---|---|---|
|  | 58 | 34.9 | 40.9 | 20.7 | 3 | 0.01 | 2.0 |

[1]Other identified compounds present in some samples are 2,3,6-trichloropyridine, 2,3,5,6-tetrachloropyridine, 2,3,4,6-tetrachloropyridine, pentachloropyriine, 2,4-dichloro-6-(trichloromethyl)pyridine, 4,5,6-trichloro-2-(trichloromethyl)pyridine, 3,5,6-trichloro-2-(trichloromethyl)pyridine, and 3,4,5,6-tetrachloro-2-(trichloromethyl)pyridine. The composition was normalized by treating all components other than 2-chloro-6-(trichloromethyl)pyridine present at the start of the run as diluents.
[2]Average for run, calculated.

What is claimed is:
1. An improved process for chlorinating 2-chloro-6-(trichloromethyl)pyridine in the liquid phase at elevated temperatures and in the presence of a metal halide catalyst to obtain a chlorination mixture containing 5,6-dichloro-2-(trichloromethyl)pyridine and 3,6-dichloro-2-(trichloromethyl)pyridine isomers, wherein the im- provement comprises controlling the ratio of said isomers by regulating the amount of hydrogen chloride present in the chlorination system by adding hydrogen chloride to obtain a mixture enriched in 5,6-dichloro-2-(trichloromethyl)pyridine or removing hydrogen chloride to obtain a mixture enriched in 3,6-dichloro-2-(trichloromethyl)pyridine.

2. A process according to claim 1 wherein hydrogen chloride is removed to obtain a mixture enriched in 3,6-dichloro-2-(trichloromethyl)pyridine.

3. A process according to claim 2 wherein the hydrogen chloride is removed by passing excess chlorine or an inert gas through the chlorination system.

4. A process according to claim 3 wherein excess chlorine is passed through the chlorination system.

5. A process according to claim 3 wherein nitrogen is passed through the chlorination system.

6. A process according to claim 2 wherein the concentration of hydrogen chloride in the vapor phase of the chlorination system is maintained at less than about 20 weight percent.

7. A process according to claim 6 wherein the concentration of hydrogen chloride in the vapor phase of the chlorination system is maintained at less than about 10 weight percent.

8. A process according to claim 2 wherein the chlorination mixture obtained contains a ratio of 5,6-dichloro-2-(trichloromethyl)pyridine to 3,6-dichloro-2-(trichloromethyl)pyridine of less than about 2.2.

9. A process according to claim 1 wherein hydrogen chloride is added to obtain a mixture enriched in 5,6-dichloro-2-(trichloromethyl)pyridine.

10. A process according to claim 9 wherein hydrogen chloride is added as a gas.

11. A process according to claim 10 wherein at least 0.25 mole of hydrogen chloride per mole of 2-chloro-6-(trichloro-methyl)pyridine present is added.

12. A process according to claim 9 wherein the chlorination mixture obtained contains a ratio of 5,6-dichloro-2-(trichloromethyl)pyridine to 3,6-dichloro-2-(trichloromethyl)pyridine of greater than about 4.5.

* * * * *

UNITED STATES PATENT AND TRADEMARK OFFICE
CERTIFICATE OF CORRECTION

PATENT NO. : 4,939,263

DATED : July 3, 1990

INVENTOR(S) : Richard K. Helling et al.

It is certified that error appears in the above-identified patent and that said Letters Patent is hereby corrected as shown below:

Col. 7, in the third table entitled "CHLORINATION RESULTS", under the subheading "Time hours", delete "58" and insert -- 48 --.

Signed and Sealed this

Twelfth Day of May, 1992

Attest:

DOUGLAS B. COMER

*Attesting Officer*     *Acting Commissioner of Patents and Trademarks*